United States Patent [19]

Baldwin et al.

[11] Patent Number: 5,830,872
[45] Date of Patent: Nov. 3, 1998

[54] ESTERS OF D-MANNOSE OR OF XYLITOL AND THEIR USE AS MEDICAMENTS

[75] Inventors: Pierre Jean Baldwin, Prouzel; Olivier Claude Eric Douillet, Agenville; Philippe René Michel Pouillart, Longueau; Gino Lino Ronco; Pierre Joseph Villa, both of Amiens, all of France

[73] Assignee: L'Associazione di volontariato "Pro La Fondazione Futuro Senza Thalassemia", Italy

[21] Appl. No.: 776,980

[22] PCT Filed: Jun. 7, 1995

[86] PCT No.: PCT/FR95/00743

§ 371 Date: Mar. 11, 1997

§ 102(e) Date: Mar. 11, 1997

[87] PCT Pub. No.: WO96/03411

PCT Pub. Date: Feb. 8, 1996

[30] Foreign Application Priority Data

Jul. 28, 1994 [FR] France .................................. 94 09348

[51] Int. Cl.$^6$ .......................... A61K 31/70; C07H 13/02; C07H 15/04; C07H 1/00
[52] U.S. Cl. ................. 514/23; 514/25; 536/4.1; 536/115; 536/119; 536/120; 536/116; 568/852
[58] Field of Search ............................ 536/4.1, 115, 119, 536/120, 116; 514/23, 25; 568/852

[56] References Cited

U.S. PATENT DOCUMENTS 3,053,677  9/1962  Touey .................................. 106/217.8
3,862,121  1/1975  Jaques et al. ........................... 536/115
5,185,436  2/1993  Villa et al. ............................... 536/119

FOREIGN PATENT DOCUMENTS 2531632   2/1984  France .
2128613   5/1984  United Kingdom .
PCT/FR8800470  9/1988  WIPO .

OTHER PUBLICATIONS

Industrial Inorganic Chemicals, vol. 76, 1971 (1 pg) No. 20 Nov. 15, 1971 Columbus Ohio.

*Primary Examiner*—John Kight
*Assistant Examiner*—Everett White
*Attorney, Agent, or Firm*—Bierman, Muserlian and Lucas

[57] ABSTRACT

Esters associating phenylacetic, 3-phenylpropionic, 4-phenylbutyric and n-butyric acids with $Su(OH)_n$ monosaccharides or sugar alcohols, of general formula (I), in which the $Su(OH)_n$ precursor is a monosaccharide or sugar alcohol, selected so that its structure or that of its derivatives ensures that internal interesterification does not take place either because the ester based on the general formula does not have a free hydroxyl grouping, or because with regard to the ester grouping, the free hydroxyl groupings are remotely located and/or badly aligned and/or bonded to a secondary carbon atom, and in which the $Su(OH)_n$ monosaccharide or sugar alcohol is preferably D-mannose carrying the ester grouping on the anomeric carbon atom or else is a pentitol, for example, xylitol carrying the ester grouping on the C-1 primary carbon atom. These novel esters are useful as drugs, in particular in the treatment of haemoglobin diseases and premalignant or malignant tumours.

17 Claims, No Drawings

ESTERS OF D-MANNOSE OR OF XYLITOL AND THEIR USE AS MEDICAMENTS

The application is a 371 of PCT/FR95/00743, which was filed Jun. 7, 1995.

The present invention relates to esters combining phenylacetic, 3-phenylpropionic, 4-phenylbutyric and n-butyric acids with D-mannose, with xylitol and with their derivatives, and to their applications as medicaments.

It is known that phenylacetic, 4-phenylbutyric and n-butyric acids and their salts stimulate the synthesis of foetal haemoglobin, in particular that of the γ chain (E. Fibach et al., Blood (1993),82 (7), 2203; S. P. Perrine et al., Biochem. Biophys. Res. Comm. (1987), 148, 694). Moreover, they induce the γ gene of human foetal haemoglobin (J. W. Zhang et al., Developmental Genetics (1990), 11, 168; J. G. Glauber et al., Molec. Cell Biol. (1991), 11, 4690). These properties have been turned to good account in the treatment of patients affected by anaemia and by β-thalassaemic syndromes (S. P. Perrine et al., N. Engl. J. Med. (1993), 328, (2), 81).

It is also known that these acids and their salts inhibit the growth and induce the differentiation of premalignant and malignant cells (D. Samid et al., Cancer Res. (1992), 52, 1988; E. Ginsburg et al., Proc. Natl. Acad. Sci. (1973), 70, 2457; K. Yamada et al., J. Cell. Physiol. (1985), 125, 235; K. N. Prasad, Life Sciences (1980), 27, 1351), in particular of leukaemic cells (S. Fisckhoff et al., Leukemia (1990), 4, 302; D. Samid et al., Cancer Res. (1992), 52, 1988).

It is also known that n-butyric acid and its salts have a very short in vivo plasma lifetime (P. Daniel et al., Clin. Chim. Acta (1989), 81, 255). It is also known that esters resulting from the combination, via a covalent bond, of this acid with D-glucose, with D-galactose, with glycerol and with their derivatives are capable, in vivo, under the effect of the enzymatic systems in man or in animals, of slowly releasing n-butyric acid with, as a result, a much longer plasma lifetime, thus providing a better bioavailability of the biologically active part (F. Pieri et al., Patent FR 871294 (1987); Patent FR 8809092 (1988); PCT 88004470 (1988); U.S. Pat. No. 071501 (1990)).

It is also known, from biological studies of the butyric esters mentioned above, that the best compound as a medicament is the monoester 3-O-n-butanoyl-1,2-O-isopropylidene-α-D-glucofuranose (P. Pouillard, Thesus, Amiens, 1990; P. Planchon, Thesus, Amiens, 1991). However, this compound, as a result of its structure exhibiting 2 hydroxyl groups OH in the region of the O-n-butanoyl group, undergoes an internal transesterification resulting, in solution, in the mixture of the 3 3-O-butanoyl, 5-O-butanoyl and 6-O-butanoyl isomers in proportions which vary according to the operating conditions. Moreover, the isomerization of this compound continues in a non-controllable way when the sample is dissolved, in particular in aqueous medium. This isomerization is in accordance with the laws of chemistry, when, in a compound, a primary hydroxyl group is sterically close to an ester group bonded to a secondary site and when this hydroxyl group has a steric orientation favourable to the attack of the neighbouring acyl group (P. Y. Goueth et al., J. Carbohydr. Chem. (1994), 13 (2), 249). It is consequently impossible to obtain this compound with a purity greater than 95%.

One of the aims of the present invention is to prepare esters combining phenylacetic, 3-phenylpropionic, 4-phenylbutyric and n-butyric acids with monosaccharides or itols (sugar-alcohols) $Su(OH)_n$ selected so that their structure or that of their derivatives prevents the internal transesterification process responsible for the isomerization, while making possible good bioavailability of the corresponding acid.

The aim is achieved according to the invention by the synthesis, for example, of esters of general formula:

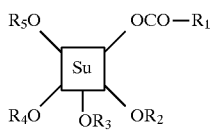

in which the monosaccharide or itol (sugar-alcohols) $Su(OH)_n$, the precursor of the compounds in accordance with the invention, is preferably D-mannose $[Su(OH)_5]$ carrying the ester group on the anomeric carbon atom or alternatively a pentitol $[Su(OH)_5]$ such as, for example, xylitol carrying the ester group on the C-1 primary carbon atom;

in which $R_1$—CO is the phenylacetyl, 3-phenylpropanoyl, 4-phenylbutanoyl or n-butanoyl group;

in which $R_2$, $R_3$, $R_4$ and $R_5$ can be the hydrogen atom or groups containing or not containing a hydrocarbon chain, which are cyclic or non-cyclic, which are saturated or unsaturated and which are branched or unbranched or alternatively selected so that $R_2$ and $R_3$ and/or $R_4$ and $R_5$ belong to an acetal group in the dioxolane form:

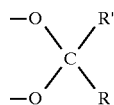

with the R—C—R' group preferably selected from phenylmethylene, methylene, cyclohexylidene or, better, isopropylidene;

and in which the internal transesterification in solution is prevented, either because the compounds do not have a free hydroxyl group or because the compounds have, with respect to the ester group, free hydroxyl groups which are distant and/or poorly oriented and/or bonded to a secondary carbon atom.

When, for example, the preparation of the esters, in accordance with the present invention, is carried out from di-O-acetals of D-mannose or of xylitol, the synthesis can take place, for example, according to Stage a, optionally followed by Stages b and/or c, as illustrated by Scheme 1 for the D-mannose compounds of type A and B and by Scheme 2 for the xylitol compounds of type C.

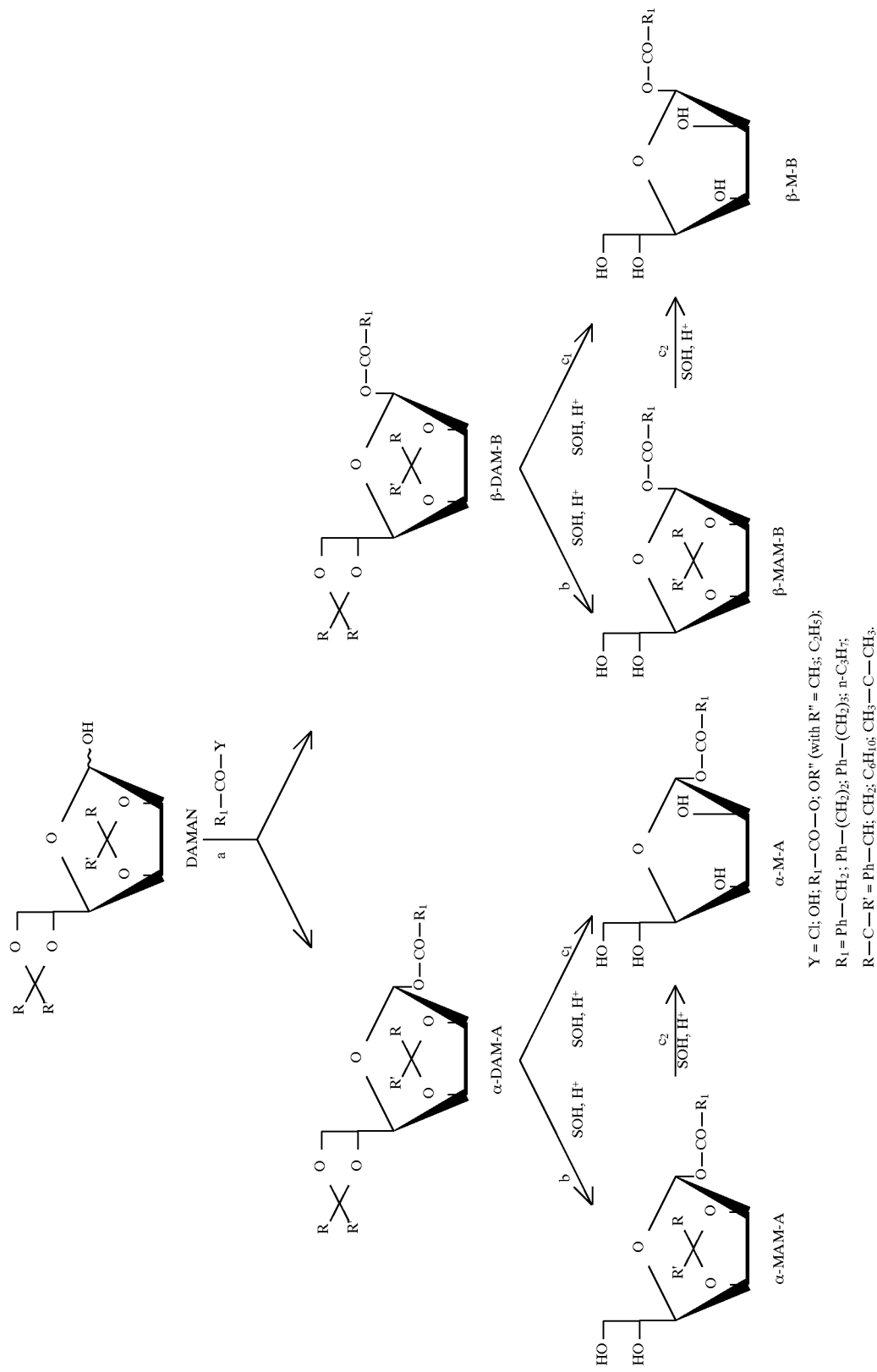

Scheme 2

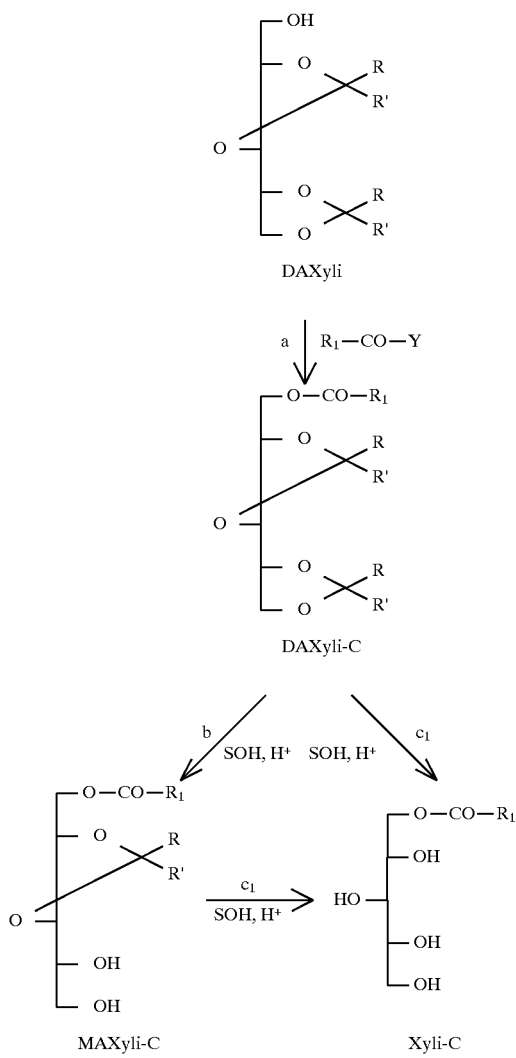

Y = Cl; OH; $R_1$—CO—O; OR" (with R" = $CH_3$; $C_2H_5$);

$R_1$ = Ph—$CH_2$; Ph—$(CH_2)_2$; Ph—$(CH_2)_3$; n-$C_3H_7$;

R—C—R' = Ph—CH; $CH_2$; $C_2H_{10}$; $CH_3$—C—$CH_3$.

Stage a: Synthesis of the α- and β-O-acyl-2,3:5,6-di-O-acetal-D-mannoside (α-DAM-A and β-DAM-B) esters and of the 1-O-acyl-2,3:4,5-di-O-acetalxylitol (DAXyli-C) esters.

These esters can be prepared, for example, by addition of an acylating agent $R_1$—CO—Y to the diacetal DAMannose and DAXylitol respectively, the preparation optionally being carried out in a solvent and in the presence of a base.

The acylating agent can be the acid (Y=OH), the acid anhydride (Y=O—CO—$R_1$), an ester (Y=OR", with R"=$CH_3$ or $C_2H_5$) or better the acid chloride (Y=Cl).

The solvent can be polar or non-polar, aliphatic or aromatic, alone or a mixture of these solvents.

The base can be a weak inorganic or organic base selected, for example, from an alkaline carbonate, pyridine or, better, triethylamine.

The acylation of the diacetal DAMannose results in the mixture of α-DAM-A and β-DAM-B anomeric esters. These esters are separated, for example, by liquid chromatography of the mixture.

Stage b: Preparation of the α- and β-O-acyl-2,3-O-acetal-D-mannoside (α-MAM-A and β-MAM-B) monoacetal esters and of the 1-O-acyl-2,3-O-acetalxylitol (MAXyli-C) esters by selective deprotection of the corresponding diacetal esters.

The selective deprotection of an acetal site according to Stage b of Schemes 1 and 2 is carried out in a hydroxylated solvent SOH by acid catalysis, either in homogeneous phase or in heterogeneous phase:

The hydroxylated solvent can be water, an alkanol, a water/alkanol mixture, an alkanol/alkanol mixture or alternatively water or alkanol in combination with a non-hydroxylated cosolvent. The alkanol can be selected, for example, from methanol, ethanol or propanol.

The cosolvent can be selected, for example, from dioxane or tetrahydrofuran.

The acid catalysis in homogeneous phase can be carried out by the addition to the medium of organic or inorganic acids. The organic acid can be selected from carboxylic or sulphonic acids, such as, for example, formic, acetic, trifluoroacetic and para-toluenesulphonic acids. The inorganic acid can be selected, for example, from sulphuric, hydrochloric, nitric and phosphoric acids. The α-MAM-A, β-MAM-B and MAXyli-C esters are obtained, in the pure state, after neutralization of the medium with an organic or inorganic base, filtration, evaporation of the solvent and purification by liquid chromatography, for example.

The acid catalysis in heterogeneous phase can be carried out by the presence, in the medium, of an acid resin or by percolation through a column filled with acid resin of the solution of ester in the hydroxylated solvent (SOH) defined above. The α-MAM-A, β-MAM-B and MAXyli-C esters are isolated in the pure state after filtration, evaporation of the solvent and purification by liquid chromatography, for example.

The D-mannose derivatives of α-MAM-A and β-MAM-B type, as well as the xylitol derivatives of MAXyli-C type, which, with respect to the ester group, have free hydroxyl groups which are distant and/or poorly oriented and/or bonded to a secondary carbon atom, cannot give rise, in solution, to an internal transesterification.

Stages $c_1$ and $c_2$: Preparation of the α- and β-O-acyl-D-mannoside (α-M-A and β-M-B) esters and of the 1-O-acylxylitol (Xyli-C) esters by deprotection of the corresponding monoacetal or diacetal esters.

The deprotection of the diacetal ester according to Stage $c_1$ or of the monoacetal ester according to Stage $c_2$ of Schemes 1 and 2 can be carried out with the same solvents (SOH) and with the same acids as those defined for Stage b of the present invention, the amount of acid, the temperature and the duration of the reaction optionally being adjusted.

The D-mannose derivatives of α-M-A type and of β-M-B type, as well as the xylitol derivatives of Xyli-C type, which, with respect to the ester group, have free hydroxyl groups which are distant and/or poorly oriented and/or bonded to a secondary carbon atom, cannot give rise, in solution, to an internal transesterification.

Another aim of the invention is the use, as medicaments, of the esters combining phenylacetic, 3-phenylpropionic, 4-phenylbutyric and n-butyric acids with D-mannose, with xylitol and with their derivatives, of general formula:

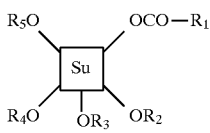

The use is targeted in particular, as with the corresponding acids and salts, and without being limiting, at haemoglobinopathies, such as, for example, anaemias, β-thalassaemia or drepanocytosis, or alternatively premalignant and malignant tumours, such as, for example, cancer of the breast, cancer of the colon or acute and chronic leukaemias.

The esters described in the present invention are also distinguished from the corresponding esters and salts by a much longer plasma life, which results in a much greater bioavailability, making it possible to envisage long-term treatments in man.

A description is given below of the preparation of esters of D-mannose, of xylitol and of their derivatives, in accordance with the present invention, by way of examples and without this being regarded as limiting.

EXAMPLE NO. 1

Preparation of the α- and β-O-acyl-2,3:5,6-di-O-isopropylidene-D-mannofuranosides (α-DAM-A and β-DAM-B)

a) Esterification of diacetonemannose with n-butanoyl chloride.

260 g (1 mol) of diacetonemannose (2,3:5,6-di-O-isopropylidene-D-mannose) are dissolved with stirring in a 3 L reactor, thermostatically controlled at 60° C., containing 2.6 L of toluene. The solution is brought to boiling point under reduced pressure at 60° C. in order to remove, by distillation, the possible traces of water in the form of a water/toluene azeotrope. After having recovered 100 mL of distillate, monitoring by the Karl-Fischer method shows that the solution in the reactor is completely anhydrous. The medium is then brought back to atmospheric pressure and, at room temperature, 106 g (1.05 mol) of triethylamine (TEA) are run in, followed, dropwise and with stirring, by 106.5 g (1 mol) of n-butanoyl chloride (duration of the addition: 10 minutes). Monitoring, carried out by VPC (OV17 column), shows the complete disappearance of the diacetonemannose after reacting for 60 minutes.

The toluene solution is filtered in order to remove the TEA hydrochloride. The filtrate, evaporated under reduced pressure, gives 332 g of crude syrupy product. The composition, determined by VPC (OV 17 column), is 90% of α anomer and 10% of β anomer.

b) Separation of the α-DAM-B and β-DAM-B anomeric butyrates.

500 mL of acetone and 300 g of neutral 60 Å silica, 35–40 mesh, are added to the 332 g of crude product above. This mixture is evaporated under reduced pressure. The sediment is transferred onto a column (diameter 40 mm) containing 700 g of silica. Elution is carried out with a hexane/acetone mixture with an increasing acetone gradient.

The following are successively isolated:
- after passage of 10 L of the hexane/acetone (97/3, v/v) mixture, 290 g of pure α anomer, which is liquid at room temperature;
  $[\alpha]_D^{23} = +43.5°$ (c=1.1; CHCl$_3$);
  the $^1$H and $^{13}$C NMR spectra (Table 1) are in accordance with the structure of the α anomer;
- after passage of 1 L of the hexane/acetone (96/4, v/v) mixture, 1.5 g of α,β mixture;
- after passage of 4 L of the hexane/acetone (90/10, v/v) mixture, 28 g of pure β anomer, which is liquid at room temperature;
  $[\alpha]_D^{20} = +23.2°$ (c=1.2; CHCl$_3$);
  the $^1$H and $^{13}$C NMR spectra (Table 2) are in accordance with the structure of the β anomer.

The total mass of the esters recovered is 319.5 g, i.e. a yield of 97% with respect to the diacetonemannose. The final yield of purified anomeric diacetonemannose butyrates is thus 88% of α ester and 9% of β ester.

c) Preparation of the α- and β-O-acyl-2,3:5,6-di-O-isopropylidene-D-mannosides (α-DAM-A and β-DAM-B), with acyl=Ph—(CH$_2$)$_n$—O and n=1, 2 or 3.

These esters are prepared under the same conditions as the corresponding n-butyrates (cf. a) but with amounts which are ten times smaller. The duration of the reaction, the α/β distribution of the anomers, the composition of the chromatography eluent for isolating the α-anomer, and the yield and the physical constants of the latter are given in the table below.

|   | | | | α-DAM-A | | | |
|---|---|---|---|---|---|---|---|
| n | Duration (h) | α/β | % Hex./Ac. (v/v) | Yd isolated (%) | [a]$_D$ in CHCl$_3$ (T°C.; c = %) | M.p. (°C.) | NMR Table |
| 1 | 2.5 | 81/19 | 95/5 | 75 | +18.2° (25; 1.6) | 79–82 | 3 |
| 2 | 2.5 | 83/17 | 95/5 | 75 | +34.6° (26; 1.6) | 105.4–105.7 | 4 |
| 3 | 4.0 | 86/14 | 94/6 | 76 | +33.3° (27; 1.1) | liquid | 5 |

The $^1$H and $^{13}$C NMR spectra are in accordance with the structure of the expected products.

EXAMPLE NO. 2

Preparation of the α-O-acyl-2,3-O-isopropylidene-D-mannofuranosides (α-MAN-A)

a) Selective acid-catalysed deprotection of the α-DAM-A butyrate.

a.1) Experimental conditions and rate of deprotection on acid resins.

20 g of Amberlite 15H$^+$ wet acid resin and 15 g of α ester are stirred in 135 mL of 96$^c$ ethanol in a round-bottomed flask thermostatically controlled at 51° C. The kinetics, monitored by HPLC (RP 18 column) quantitative determination of samples taken at intervals, show that the deprotection rate constant according to the pseudo-first-order law is k=1.10×10$^{-2}$ min$^{-1}$, which corresponds to a degree of progression of 93% after reacting for 4 hours. HPLC (RP 18 column) analysis of the sample taken after 4 hours shows the presence of 2 signals of relative intensities 93/7. The more intense corresponds to a more polar product identified, by the analyses described hereinbelow in 2-b, as being O-n-butanoyl-2,3-O-isopropylidene-α-D-mannoside.

composition of the chromatography eluent, the yield and the physical constants are given in the table below.

| n | Duration (h) | Hex./Ac. (v/v) | Yd isolated (%) | $[a]_D$ in $CHCl_3$ (T°C.; c = %) | M.p. (°C.) | NMR Table |
|---|---|---|---|---|---|---|
| 1 | 4.0 | 75/25 | 75 | +32.2° (25; 1.6) | liquid | 7 |
| 2 | 4.5 | 70/30 | 77 | +34.6° (26; 1.6) | 30.5–33.6 | 8 |
| 3 | 3.5 | 75/25 | 77 | +33.3° (27; 1.1) | 70.2–72.6 | 9 |

Under these experimental conditions, there is highly selective deprotection of the 5,6-O-isopropylidene group.

a.2) Quantitative deprotection of the α-DAM-A butyrate on acid resins.

The procedure is as in a.1, with 2.25 L of 96° ethanol, 187.5 g of acid resin and 250 g of α-DAM-A ester. After reacting for 4 hours, the mixture is filtered and the resins are rinsed with 2 times 200 mL of 96° ethanol. The evaporation of the combined alcoholic solutions makes it possible to recover 220 g of solid residue.

a.3) Selective acid-catalysed deprotection of the α-DAM-A butyrate in homogeneous medium.

The deprotection of the ester was also carried out in homogeneous solution in a round-bottomed flask, thermostatically controlled at 30° C., containing 100 mL of 96° ethanol, or 100 mL of dioxane/water (80/20, v/v) solvent, with 0.2N $H_2SO_4$ and 15 g of α-DAM-A butyrate.

The degree of deprotection exceeds 90% after reacting for 4 hours. The extraction of the product involves neutralization by an aqueous sodium hydroxide solution. To prevent deesterification of the product, addition of the base must be performed at low temperature (0° to 10° C.) and halted as soon as the pH of the medium reaches 7 units. The crude product is isolated after separation of the sodium sulphate by filtration and evaporation of the solvent under reduced pressure.

b) Purification of the α-MAM-A butyrate.

500 mL of toluene and 250 g of neutral 60 Å silica, 35–40 mesh, are added to the 220 g of solid residue above. This mixture is evaporated under reduced pressure. The sediment is transferred onto a column (diameter 40 mm) containing 750 g of silica. Elution is carried out with a hexane/acetone mixture with an increasing acetone gradient.

The following are successively isolated:

after passage of 4.5 L of hexane/acetone (85/15, v/v) mixture, 15 g of α-DAM-A ester;

after passage of 6 L of hexane/acetone (70/30, v/v) mixture, 190 g of O-n-butanoyl-2,3-O-isopropylidene-α-D-mannoside-α-MAM-A [sic];

$[\alpha]_D^{22}$=+54.6° (c=1.2; $CHCl_3$);

M.p.=79° C.;

the $^1H$ and $^{13}C$ NMR spectra (Table 6) are in accordance with the structure of the expected product;

after passage of 1 L of the hexane/acetone (50/50, v/v) mixture and then of 2 L of pure acetone, 6 g of mixture mostly containing O-n-butanoyl-α-D-mannoside and then 3 g of pure O-n-butanoyl-α-Dmannoside from HPLC analysis.

c) Preparations of the O-acyl-2,3-O-isopropylidene-α-D-mannofuranoside (α-MAM-A) esters, with acyl=Ph—$(CH_2)_n$—CO and n=1, 2 or 3.

These esters are prepared under the same conditions as the corresponding n-butyrates (cf. a.2) but with amounts which are ten times smaller. The duration of the reaction, the The $^1H$ and $^{13}C$ NMR spectra are in accordance with the nature of the expected products.

EXAMPLE NO. 3

Preparation of the 1-O-acyl-2,3:4,5-di-O-isopropylidenexylitol (DAxyli -C)

a) Esterification of diacetonexylitol with n-butanoyl chloride.

100 g (0.43 mol) of diacetonexylitol (2,3:4,5-di-O-isopropylidenexylitol) are dissolved with stirring in a 3 L reactor, thermostatically controlled at 60° C., containing 800 mL of toluene. The solution is brought to boiling point under reduced pressure at 60° C. in order to remove, by distillation, the possible traces of water in the form of a water/toluene azeotrope. After having recovered 40 mL of distillate, monitoring by the Karl-Fischer method shows that the solution in the reactor is completely anhydrous. The medium is then brought back to atmospheric pressure and, at room temperature, 47.1 g (0.47 mol) of triethylamine (TEA) are run in, followed, dropwise and with stirring, by 45.9 g (0.43 mol) of butanoyl chloride (duration of the addition 7 minutes). Monitoring, carried out by VPC (OV17 column), shows the complete disappearance of the diacetonexylitol after reacting for 4 hours.

The toluene solution is filtered in order to remove the TEA hydrochloride. The filtrate, evaporated under reduced pressure, gives 131 g of crude syrupy product.

b) Purification of the DAXyli-C butyrate.

250 mL of acetone and 100 g of neutral 60 Å silica, 35–40 mesh, are added to the 131 g of crude product above. This mixture is evaporated under reduced pressure. The sediment is transferred onto a column (diameter 40 mm) containing 400 g of silica. Elution is carried out with a hexane/acetone mixture with an increasing acetone gradient.

After passage of the hexane/acetone (98/2, v/v) mixture, 108.7 g of pure ester are isolated, i.e. a yield of 84% with respect to the diacetonexylitol;

$[\alpha]_D^{23}$=−0.3° (c=1.7; $CHCl_3$);

the $^1H$ and $^{13}C$ NMR spectra (Table 10) are in accordance with the structure of the α anomer.

c) Preparation of the 1-O-acyl-2,3:4,5-di-O-isopropylidenexylitol esters, with acyl=Ph—$(CH_2)_n$—O and n=1, 2 or 3.

These esters are prepared are prepared under the same conditions as the corresponding n-butyrates (cf. a) but with amounts which are ten times smaller. These compounds are liquid at room temperature. The duration of the reaction, the composition of the chromatography eluent, the yields and the physical constants are given in the table below.

| n | Duration (h) | Hex./Ac. (v/v) | Yd isolated (%) | $[\alpha]_D$ in CHCl$_3$ (T°C.; c = %) | NMR Table |
|---|---|---|---|---|---|
| 1 | 5.0 | 90/10 | 86 | −1.6° (29; 1.0) | 11 |
| 2 | 3.0 | 95/5 | 91 | −1.1° (29; 1.0) | 12 |
| 3 | 4.0 | 90/10 | 89 | −1.7° (29; 1.1) | 13 |

The $^1$H and 13 C NMR spectra are in accordance with the structure of the expected products.

EXAMPLE NO. 4

Preparation of the 1-O-acyl-2,3-O-isopropylidenexylitol (MAXyli-C) and of the 1-O-acylxylitol (Xyli -C)

a) Selective and complete acid-catalysed deprotections of the DAXyli-C butyrate.

200 g of Amberlyst 15H$^+$ wet acid resin and 100 g of ester are stirred in 800 mL of 96° ethanol in a round-bottomed flask thermostatically controlled at 52° C. The kinetics, monitored by HPLC (RP 18 column) quantitative determination of samples taken at intervals, show that there is a degree of progression of 98% after reacting for 4 hours. HPLC analysis of the sample taken shows the presence of 2 signals of relative intensities 7/3. The more intense corresponds to a more polar product identified, by the analyses described hereinbelow in 4-b, as being 1-O-n-butanoylxylitol. After reacting for 4 hours, the mixture is filtered and the resins are rinsed with 2 times 200 mL of 96° ethanol. Evaporation of the combined alcoholic solutions makes it possible to recover 79 g of syrupy liquid.

b) Separation of the MAXyli-C and Xyli-C butyrates.

150 mL of $_{96}$c ethanol and 80 g of neutral 60 Å0 silica, 35–40 mesh, are added to the 79 g of crude product above. This mixture is evaporated under reduced pressure. The sediment is transferred onto a column (diameter 30 mm) containing 320 g of silica. Elution is carried out with an industrial hexane/acetone mixture with an increasing acetone gradient.

The following are successively isolated:

after passage of 7 L of the hexane/acetone (75/25, v/v) mixture, 25 g of pure MAXyli-C ester, which is liquid at room temperature;
$[\alpha]_D^{26}$=+0.3° (c=1.2; CHCl$_3$);
the $^1$H and $^{13}$C NMR spectra (Table 14) are in accordance with the structure of the expected product;

after passage of the hexane/acetone (20/80, v/v) mixture, 46.8 g of pure Xyli-C ester, which is liquid at room temperature;
$[\alpha]_D^{26}$=+1.3° (1.1; CHCl$_3$);
the $^1$H and $^{13}$C NMR spectra (Table 15) are in accordance with the structure of the expected product.

c) Preparation of the 1-O-acyl-2,3-O-isopropylidenexylitol (MAXyli-C) and 1-O-acylxylitol (Xyli-C) esters, with acyl=Ph—(CH$_2$)$_n$—O and n=1, 2 or 3.

These esters are prepared under the same conditions as the corresponding n-butyrates (cf. a) but with amounts which are ten times smaller. The duration of the reaction, the distribution of the MAXyli-C and Xyli-C esters, the composition of the eluent in order to isolate each of them, and the yield and the physical constants of these compounds are given in the table below.

| n | Duration (h) | Product | Hex./Ac. (v/v) | Yd isolated (%) | $[\alpha]_D$ in MeOH (T° C.; c = %) | M.p. (°C.) | NMR Table |
|---|---|---|---|---|---|---|---|
| 1 | 2.5 | MAXyli-C | 88/22 | 32 | −4.1° (30; 1.2) | liquid | 16 |
|   |     | Xyli-C   | 40/60 | 56 | −2.0° (30; 1.0) | 66.8–69.3 | 17 |
| 2 | 3.0 | MAXyli-C | 75/25 | 36 | −5.5° (31; 1.0) | liquid | 18 |
|   |     | Xyli-C   | 35/65 | 60 | −1.7° (30; 1.1) | liquid | 19 |
| 3 | 2.5 | MAXyli-C | 75/25 | 36 | −3.2° (31; 1.8) | liquid | 20 |
|   |     | Xyli-C   | 25/75 | 62 | −3.0° (30; 1.0) | 39.5–42.8 | 21 |

The $^1$H and $^{13}$C NMR spectra are in accordance with the structure of the expected products.

EXAMPLE NO. 5

Chemical stability of the esters in aqueous medium

The α-O-acyl-2,3-O-isopropylidenemannoside esters described in Example No. 2, as well as the 1-O-acyl-2,3-O-isopropylidenexylitol and 1-O-acylxylitol esters described in Example No. 4, were subjected to prolonged monitoring of stability in solution under the conditions below:

1. in distilled water (pH=6.5) at 4° C. and at 25° C.;
2. in a 50/50 (v/v) water/ethanol mixture at 25° C.;
3. in distilled water with 0.2 mol.L$^{-1}$ CO$_3$HNa (pH=8.1) at 25° C.

Results

Under the conditions 1. and 2., monitoring carried out by HPLC (RP 18 column, water/acetone eluent) shows that the loss of ester by hydrolysis is less than 1% after one month in solution. In addition, evaporation after one month, followed by liquid chromatography, makes it possible to recover the pure ester, from its physical and spectroscopic constants, the mass of which represents 98% of the mass of the ester initially dissolved.

Under the conditions 3., monitoring operations carried out by HPLC, as for 1. and 2., show a faster deesterification of the esters than under the above conditions, because of the basicity of the medium (pH=8.1, against 6.5 under the conditions 1.). This deesterification takes place at a rate in the region of that observed for 3-O-n-butanoyl-1,2-O-isopropylidene-α-D-glucofuranose under the same conditions (Goueth et al., J. Carbohydr. Chem. (1994), 13 (2), 249), i.e. 20% in 95 hours, against 15 to 25% for the esters studied. However, for each of the esters described here, the ester fraction recovered after 95 hours has the same physical and spectroscopic constants as the product initially dissolved, whereas, for 3-O-n-butanoyl-1,2-O-isopropylidene-α-D-glucofuranose, the non-deesterified fraction is composed of 6% of the initial ester, 90% of the 6-O-n-butanoyl isomer and 4% of the 5-O-n-butanoyl isomer.

EXAMPLE NO. 6

Demonstration of the antiproliferative and cell maturation properties of the α-MAM-A, MAXyli-C and Xyli-C butyric esters (R$_1$=n-C$_3$H$_7$) on lines responsible for acute myeloid leukaemia The tests were carried out on stabilized cell lines (HL 60 and others) in the absence of growth factors. The concentrations of butyric derivatives vary from 0.5 to 1 mM.

The following parameters were evaluated by "FASC Scan" scanning and flow cytometry:

incorporation of tritiated thymidine (exploration of cell metabolism);

incorporation of propylium iodide (determination of the phase of the cell cycle);

evaluation of the level of cells in the apoptosis phase (programmed cell death);

evaluation of cell maturation (quantitative determination of the surface antigens by specific monoclonal antibodies).

The antiproliferative properties are demonstrated by the data in the table below on the percentage of inhibition of cell growth and on the percentage of cells in apoptosis.

| Butyric compounds ($R_1$ = n-$C_3H_7$) | % of inhibition of growth HL 60 (n days) | % of apoptosis HL 60 and others (3 days) |
|---|---|---|
| α-MAM-A | 40 (2 d.) | 13 to 84, depending on the line |
|  | 80 (5 d.) |  |
| MAXyli-C | 80 (3 d.) | 27 to 96, depending on the line |
|  | 90 (4 d.) |  |
| Xyli-C | 70 (5 d.) | 10 to 35, depending on the line |

The maturation of the myeloid cells is evaluated by the expression of the specific antigens CD 15, CD 11a and CD 11b. The three above products, at a concentration of 1 mM, cause only a marginal increase in the specific antigens for maturation.

EXAMPLE NO. 7

Demonstration of the effect of the α-MAC-A and Xyli-C butyric esters ($R_1$=n-$C_3H_7$) on the synthesis of foetal haemoglobin The tests were carried out on erythroleukaemic cell lines in the presence of normal human serum.

The following parameters were evaluated:

level of γ chain of the haemoglobin (immunological quantitative determination by double antigen antibody reaction and by immunocytochemical quantitative determination in the presence of alkaline phosphatase-anti-alkaline phosphatase A.P.A.A.P.);

level of mRNA of the γ chains (Northern Blot Analysis).

It is observed that the α-MAM-A and Xyli-C esters, at the respective concentrations of 0.70 mM and 0.35 mM, increase the level of γ chain of the haemoglobin.

In the presence of A.P.A.A.P., this level changes from 10% without ester to 22% with α-MAM-A and to 17% with Xyli-C. The test for detection of the mRNAs of the γ chains in the presence of the above esters shows in a very significant way the increase in the mRNAs.

TABLE 1

$^1$H and $^{13}$C NMR spectra of O-n-butanoyl-2,3:5,6-di-O-isopropylidene-α-D-mannoside.

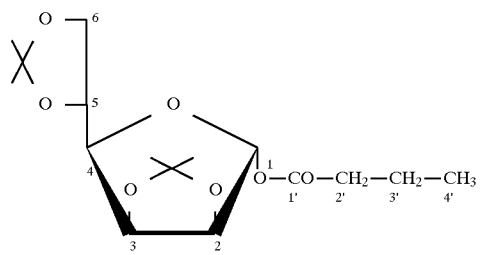

| C | δ (ppm) | H | δ (ppm) | J (Hz) |
|---|---|---|---|---|
| $C_1$ | 99.4 | $H_1$ | 5.94 | s | $J_{1-2} = 0$ |
| $C_2$ | 83.9 | $H_2$ | 4.50 | d | $J_{2-3} = 5.8$ |
| $C_3$ | 78.2 | $H_3$ | 4.67 | dd | $J_{3-4} = 3.7$ |
| $C_4$ | 81.1 | $H_4$ | 3.82 | m | $J_{4-5} = 4.4$ |
| $C_5$ | 71.8 | $H_5$ | 4.20 | m | $J_{5-6a} = 6.2$ |
| $C_6$ | 65.7 | $H_{6a}$ | 3.90 | dd | $J_{6a-6b} = 8.7$ |
| $C_{iso}$ | 112.0 | $H_{6b}$ | 3.82 | m | $J_{5-6b} = 7.6$ |
| $C_{iso}$ | 108.1 | $CH_{3\ iso}$ | 1.29 | s | — |
| $CH_3$ | 25.8 | $CH_{3\ iso}$ | 1.26 | s | — |
| $CH_3$ | 24.8 | $CH_{3\ iso}$ | 1.18 | s | — |
| $CH_3$ | 24.0 | $CH_{3\ iso}$ | 1.15 | s | — |
| $CH_3$ | 23.5 | $H_2'$ | 2.10 | t | $J_{2'-3'} = 7.2$ |
| $C_{1'}$ | 170.7 | $H_{3'}$ | 1.46 | q | $J_{3'-4'} = 7.4$ |
| $C_{2'}$ | 34.9 | $H_{4'}$ | 0.76 | t | — |
| $C_{3'}$ | 17.1 |  |  |  |
| $C_{4'}$ | 12.4 |  |  |  |

(Solvent: $CDCl_3$; chemical shift δ with respect to the TMS signal).

TABLE 2

$^1$H and $^{13}$C NMR spectra of O-n-butanoyl-2,3:5,6-di-O-isopropylidene-β-D-mannoside.

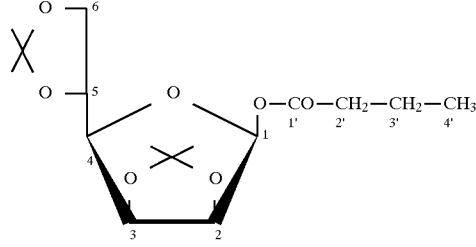

| C | δ (ppm) | H | δ (ppm) | J (Hz) |
|---|---|---|---|---|
| $C_1$ | 95.4 | $H_1$ | 5.66 | d | $J_{1-2} = 2.9$ |
| $C_2$ | 77.8 | $H_2$ | 4.63 | m | $J_{2-3} = $ n.d. |
| $C_3$ | 78.4 | $H_3$ | 4.63 | m | $J_{3-4} = 2.8$ |
| $C_4$ | 77.4 | $H_4$ | 3.62 | dd | $J_{4-5} = 7.8$ |
| $C_5$ | 72.1 | $H_5$ | 4.24 | m | $J_{5-6a} = $ n.d. |
| $C_6$ | 65.7 | $H_{6a}$ | 3.87 |  | $J_{6a-6b} = $ n.d. |
| $C_{iso}$ | 113.2 | $H_{6b}$ | AA'X | Syst. | $J_{5-6b} = $ n.d. |
| $C_{iso}$ | 108.3 | $CH_{3\ iso}$ | 1.32 | s | — |
| $CH_3$ | 25.9 | $CH_{3\ iso}$ | 1.26 | s | — |
| $CH_3$ | 24.6 | $CH_{3\ iso}$ | 1.17 | s | — |
| $CH_3$ | 24.3 | $CH_{3\ iso}$ | 1.17 | s | — |
| $CH_3$ | 24.2 | $H_2'$ | 2.16 | t | $J_{2'-3'} = 7.4$ |
| $C_{1'}$ | 170.6 | $H_{3'}$ | 1.48 | q | $J_{3'-4'} = 7.4$ |
| $C_{2'}$ | 34.9 | $H_{4'}$ | 0.76 | t | — |
| $C_{3'}$ | 17.0 |  |  |  |
| $C_{4'}$ | 12.5 |  |  |  |

(Solvent: $CDCl_3$; chemical shift δ with respect to the TMS signal).

TABLE 3

$^1$H and $^{13}$C NMR spectra of O-phenylacetyl-2,3:5,6-di-O-isopropylidene-α-D-mannoside.

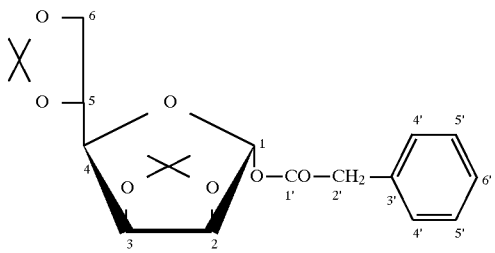

| C | δ (ppm) | H | δ (ppm) | | J (Hz) |
|---|---------|---|---------|---|--------|
| $C_1$ | 100.9 | $H_1$ | 6.11 | s | $J_{1-2} = 0$ |
| $C_2$ | 84.9 | $H_2$ | 4.63 | d | $J_{2-3} = 5.8$ |
| $C_3$ | 79.3 | $H_3$ | 4.78 | dd | $J_{3-4} = 3.5$ |
| $C_4$ | 82.4 | $H_4$ | 3.88 | m | $J_{4-5} = 8.0$ |
| $C_5$ | 72.7 | $H_5$ | 4.35 | m | $J_{5-6a} = 6.2$ |
| $C_6$ | 66.6 | $H_{6a}$ | 4.05 | dd | $J_{6a-6b} = 8.8$ |
| $C_{iso}$ | 113.2 | $H_{6b}$ | 3.93 | m | $J_{5-6b} = 4.4$ |
| $C_{iso}$ | 109.2 | $CH_{3\ iso}$ | 1.43 | s | — |
| $CH_3$ | 26.8 | $CH_{3\ iso}$ | 1.40 | s | — |
| $CH_3$ | 25.9 | $CH_{3\ iso}$ | 1.34 | s | — |
| $CH_3$ | 25.1 | $CH_{3\ iso}$ | 1.29 | s | — |
| $CH_3$ | 24.6 | $H_{2'}$ | 2.13 | s | — |
| $C_{1'}$ | 169.7 | $H_{4'}$ | 7.22 | m | — |
| $C_{2'}$ | 41.3 | $H_{5'}$ | to | | — |
| $C_{3'}$ | 133.4 | $H_{6'}$ | 7.33 | | |
| $C_{4'}$ | 129.0 | | | | |
| $C_{5'}$ | 128.6 | | | | |
| $C_{6'}$ | 127.2 | | | | |

(Solvent: $CDCl_3$; chemical shift δ with respect to the TMS signal).

TABLE 4

$^1$H and $^{13}$C NMR spectra of O-3'-phenylpropanoyl-2,3:5,6-di-O-isopropylidene-α-D-mannoside.

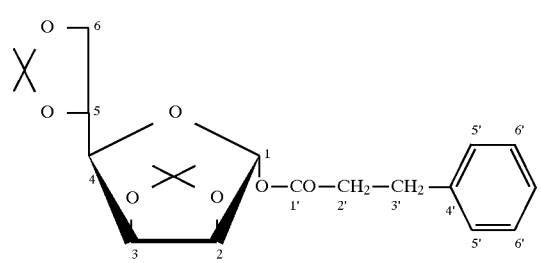

| C | δ (ppm) | H | δ (ppm) | | J (Hz) |
|---|---------|---|---------|---|--------|
| $C_1$ | 100.9 | $H_1$ | 6.08 | s | $J_{1-2} = 0$ |
| $C_2$ | 85.0 | $H_2$ | 4.54 | d | $J_{2-3} = 5.8$ |
| $C_3$ | 79.2 | $H_3$ | 4.74 | dd | $J_{3-4} = 3.6$ |
| $C_4$ | 82.3 | $H_4$ | 3.91 | m | $J_{4-5} = 7.8$ |
| $C_5$ | 72.8 | $H_5$ | 4.35 | m | $J_{5-6a} = 6.2$ |
| $C_6$ | 66.2 | $H_{6a}$ | 4.06 | dd | $J_{6a-6b} = 8.8$ |
| $C_{iso}$ | 113.1 | $H_{6b}$ | 3.97 | m | $J_{5-6b} = 4.5$ |
| $C_{iso}$ | 109.2 | $CH_{3\ iso}$ | 1.44 | s | — |
| $CH_3$ | 26.8 | $CH_{3\ iso}$ | 1.42 | s | — |
| $CH_3$ | 26.6 | $CH_{3\ iso}$ | 1.34 | s | — |
| $CH_3$ | 25.1 | $CH_{3\ iso}$ | 1.29 | s | — |
| $CH_3$ | 24.9 | $H_{2'}$ | 2.92 | t | $J_{2'-3'} = 7.4$ |
| $C_{1'}$ | 171.1 | $H_{3'}$ | 2.62 | t | — |
| $C_{2'}$ | 35.9 | $H_{5'}$ | 7.27 | m | — |
| $C_{3'}$ | 30.7 | $H_{6'}$ | to | | |

TABLE 4-continued $^1$H and $^{13}$C NMR spectra of O-3'-phenylpropanoyl-2,3:5,6-di-O-isopropylidene-α-D-mannoside.

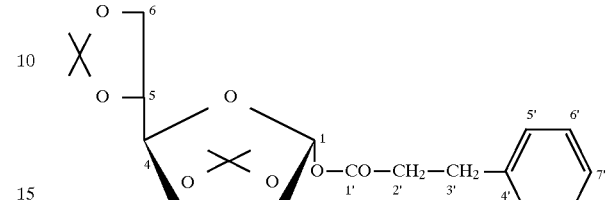

| C | δ (ppm) | H | δ (ppm) | J (Hz) |
|---|---------|---|---------|--------|
| $C_{4'}$ | 140.0 | $H_{7'}$ | 7.18 | — |
| $C_{5'}$ | 128.4 | | | |
| $C_{6'}$ | 128.1 | | | |
| $C_{7'}$ | 126.3 | | | |

(Solvent: $CDCl_3$; chemical shift δ with respect to the TMS signal).

TABLE 5

$^1$H and $^{13}$C NMR spectra of O-4'-phenylbutanoyl-2,3:5,6-di-O-isopropylidene-α-D-mannoside.

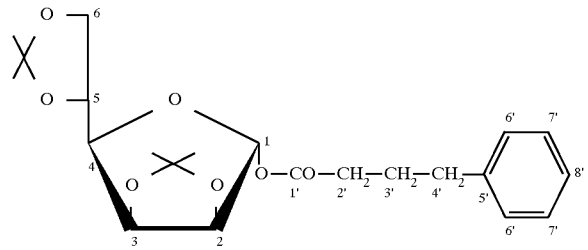

| C | δ (ppm) | H | δ (ppm) | | J (Hz) |
|---|---------|---|---------|---|--------|
| $C_1$ | 100.7 | $H_1$ | 6.11 | s | $J_{1-2} = 0$ |
| $C_2$ | 85.0 | $H_2$ | 4.66 | d | $J_{2-3} = 5.8$ |
| $C_3$ | 79.3 | $H_3$ | 4.84 | dd | $J_{3-4} = 3.6$ |
| $C_4$ | 82.3 | $H_4$ | 4.01 | m | $J_{4-5} = 7.8$ |
| $C_5$ | 72.8 | $H_5$ | 4.40 | m | $J_{5-6a} = 6.1$ |
| $C_6$ | 66.7 | $H_{6a}$ | 4.09 | dd | $J_{6a-6b} = 8.7$ |
| $C_{iso}$ | 113.2 | $H_{6b}$ | 4.03 | m | $J_{5-6b} = 4.8$ |
| $C_{iso}$ | 109.2 | $CH_{3\ iso}$ | 1.45 | s | — |
| $CH_3$ | 26.8 | $CH_{3\ iso}$ | 1.42 | s | — |
| $CH_3$ | 26.0 | $CH_{3\ iso}$ | 1.34 | s | — |
| $CH_3$ | 25.1 | $CH_{3\ iso}$ | 1.30 | s | — |
| $CH_3$ | 24.6 | $H_{2'}$ | 2.62 | t | $J_{2'-3'} = 7.7$ |
| $C_{1'}$ | 171.6 | $H_{3'}$ | 1.92 | t | $J_{3'-4'} = 7.4$ |
| $C_{2'}$ | 34.9 | $H_{4'}$ | 2.29 | | — |
| $C_{3'}$ | 33.3 | $H_{6'}$ | 7.29 | m | — |
| $C_{4'}$ | 25.9 | $H_{7'}$ | to | | — |
| $C_{5'}$ | 141.0 | $H_{8'}$ | 7.13 | | — |
| $C_{6'}$ | 128.3 | | | | |
| $C_{7'}$ | 126.3 | | | | |
| $C_{8'}$ | 126.0 | | | | |

(Solvent: $CDCl_3$; chemical shift δ with respect to the TMS signal).

TABLE 6

$^1$H and $^{13}$C NMR spectra of O-n-butanoyl-2,3-O-isopropylidene-α-D-mannoside.

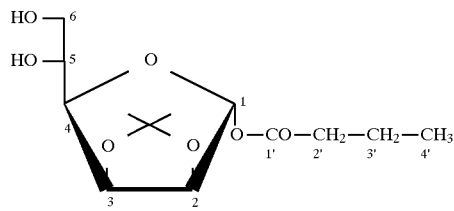

| C | δ (ppm) | H | δ (ppm) | J (Hz) |
|---|---|---|---|---|
| $C_1$ | 99.4 | $H_1$ | 6.05 | s | $J_{1-2} = 0$ |
| $C_2$ | 83.7 | $H_2$ | 4.58 | d | $J_{2-3} = 5.9$ |
| $C_3$ | 78.7 | $H_3$ | 4.81 | dd | $J_{3-4} = 3.4$ |
| $C_4$ | 80.3 | $H_4$ | 3.94 | dd | $J_{4-5} = 8.5$ |
| $C_5$ | 68.8 | $H_5$ | 3.91 | m | $J_{5-6a} = 7.9$ |
| $C_6$ | 63.1 | $H_{6a}$ | 3.73 | dd | $J_{6a-6b}$ = n.d. |
| $C_{iso}$ | 112.2 | $H_{6b}$ | 3.59 | dd | $J_{5-6b}$ = n.d. |
| $CH_3$ | 24.9 | $CH_{3\,iso}$ | 1.38 | s | — |
| $CH_3$ | 23.7 | $CH_{3\,iso}$ | 1.24 | s | — |
| $C_{1'}$ | 171.1 | $H_{2'}$ | 2.17 | t | $J_{2'-3'} = 7.4$ |
| $C_{2'}$ | 35.1 | $H_{3'}$ | 1.53 | q | $J_{3'-4'} = 7.4$ |
| $C_{3'}$ | 17.2 | $H_{4'}$ | 0.83 | t | — |
| $C_{4'}$ | 12.5 | OH | 3.33 | s | — |
|  |  | OH | 2.85 | s | — |

(Solvent: $CDCl_3$; chemical shift δ with respect to the TMS signal).

TABLE 7

$^1$H and $^{13}$C NMR spectra of O-phenylacetyl-2,3-O-isopropylidene-α-D-mannoside.

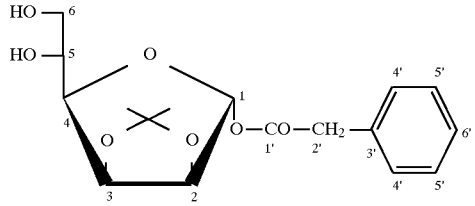

| C | δ (ppm) | H | δ (ppm) | J (Hz) |
|---|---|---|---|---|
| $C_1$ | 100.6 | $H_1$ | 6.15 | s | $J_{1-2} = 0$ |
| $C_2$ | 84.6 | $H_2$ | 4.55 | d | $J_{2-3} = 5.9$ |
| $C_3$ | 79.6 | $H_3$ | 4.80 | dd | $J_{3-4} = 2.5$ |
| $C_4$ | 81.3 | $H_4$ | 4.00 | m | $J_{4-5} = 7.7$ |
| $C_5$ | 69.8 | $H_5$ | 3.95 | m | $J_{5-6a} = 2.4$ |
| $C_6$ | 64.1 | $H_{6a}$ | 3.83 | dd | $J_{6a-6b} = 11.5$ |
| $C_{iso}$ | 113.1 | $H_{6b}$ | 3.62 | m | $J_{5-6b} = 4.7$ |
| $CH_3$ | 26.0 | $CH_{3\,iso}$ | 1.45 | s | — |
| $CH_3$ | 24.7 | $CH_{3\,iso}$ | 1.28 | s | — |
| $C_{1'}$ | 171.5 | $H_{2'}$ | 2.92 | s | — |
| $C_{2'}$ | 41.3 | $H_{4'}$ | 7.25 | m | — |
| $C_{3'}$ | 133.7 | $H_{5'}$ | to |  | — |
| $C_{4'}$ | 128.4 | $H_{6'}$ | 7.12 |  | — |
| $C_{5'}$ | 128.2 | $OH_{5,6}$ | 2.80 | m | — |
| $C_{6'}$ | 125.9 |  |  |  |  |

(Solvent: $CDCl_3$; chemical shift δ with respect to the TMS signal).

TABLE 8

$^1$H and $^{13}$C NMR spectra of O-3'-phenylpropanoyl-2,3-O-isopropylidene-α-D-mannoside.

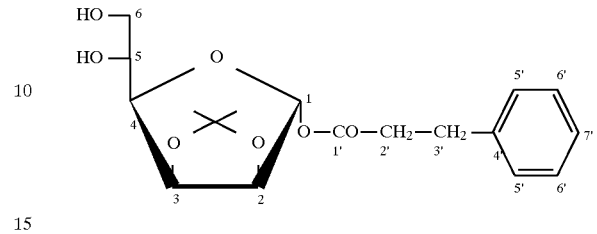

| C | δ (ppm) | H | δ (ppm) | J (Hz) |
|---|---|---|---|---|
| $C_1$ | 100.6 | $H_1$ | 6.10 | s | $J_{1-2} = 0$ |
| $C_2$ | 84.7 | $H_2$ | 4.50 | d | $J_{2-3} = 5.8$ |
| $C_3$ | 79.7 | $H_3$ | 4.77 | dd | $J_{3-4} = 2.6$ |
| $C_4$ | 81.3 | $H_4$ | 3.94 | m | $J_{4-5} = 7.9$ |
| $C_5$ | 69.9 | $H_5$ | 3.91 | m | $J_{5-6a} = 2.3$ |
| $C_6$ | 64.0 | $H_{6a}$ | 3.77 | dd | $J_{6a-6b} = 11.5$ |
| $C_{iso}$ | 113.2 | $H_{6b}$ | 3.61 | m | $J_{5-6b} = 4.6$ |
| $CH_3$ | 25.9 | $CH_{3\,iso}$ | 1.44 | s | — |
| $CH_3$ | 24.7 | $CH_{3\,iso}$ | 1.29 | s | — |
| $C_{1'}$ | 171.1 | $H_{2'}$ | 2.90 | t | $J_{2'-3'} = 7.5$ |
| $C_{2'}$ | 35.7 | $H_{3'}$ | 2.60 | t | — |
| $C_{3'}$ | 30.6 | $H_{5'}$ | 7.27 | m | — |
| $C_{4'}$ | 140.0 | $H_{6'}$ | to |  | — |
| $C_{5'}$ | 128.4 | $H_{7'}$ | 7.03 |  | — |
| $C_{6'}$ | 128.2 | $OH_{5,6}$ | 3.15 | m | — |
| $C_{7'}$ | 126.3 |  |  |  |  |

(Solvent: $CDCl_3$; chemical shift δ with respect to the TMS signal).

TABLE 9

$^1$H and $^{13}$C NMR spectra of O-4'-phenylbutanoyl-2,3-O-isopropylidene-α-D-mannoside.

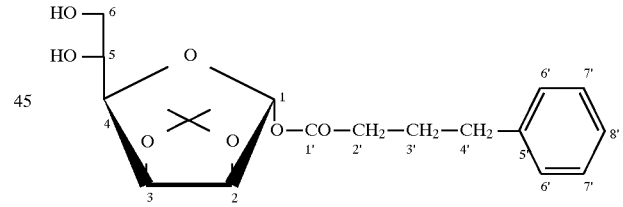

| C | δ (ppm) | H | δ (ppm) | J (Hz) |
|---|---|---|---|---|
| $C_1$ | 100.5 | $H_1$ | 6.16 | s | $J_{1-2} = 0$ |
| $C_2$ | 84.8 | $H_2$ | 4.64 | d | $J_{2-3} = 5.9$ |
| $C_3$ | 79.7 | $H_3$ | 4.86 | dd | $J_{3-4} = 3.5$ |
| $C_4$ | 81.3 | $H_4$ | 4.03 | m | $J_{4-5} = 8.3$ |
| $C_5$ | 69.9 | $H_5$ | 3.98 | m | $J_{5-6a} = 2.8$ |
| $C_6$ | 64.0 | $H_{6a}$ | 3.81 | dd | $J_{6a-6b} = 11.5$ |
| $C_{iso}$ | 113.2 | $H_{6b}$ | 4.62 | m | $J_{5-6b} = 5.3$ |
| $CH_3$ | 26.0 | $CH_{3\,iso}$ | 1.45 | s | — |
| $CH_3$ | 24.7 | $CH_{3\,iso}$ | 1.30 | s | — |
| $C_{1'}$ | 171.7 | $H_{2'}$ | 2.60 | t | $J_{2'-3'} = 7.5$ |
| $C_{2'}$ | 34.9 | $H_{3'}$ | 1.91 | t | $J_{3'-4'} = 7.4$ |
| $C_{3'}$ | 33.4 | $H_{4'}$ | 2.27 |  | — |
| $C_{4'}$ | 25.9 | $H_{6'}$ | 7.27 | m | — |
| $C_{5'}$ | 141.0 | $H_{7'}$ | to |  | — |
| $C_{6'}$ | 128.3 | $H_{8'}$ | 7.11 |  | — |
| $C_{7'}$ | 128.3 | $OH_{5,6}$ | 3.35 | m | — |
| $C_{8'}$ | 126.0 |  |  |  |  |

(Solvent: $CDCl_3$; chemical shift δ with respect to the TMS signal).

TABLE 10

$^1$H and $^{13}$C NMR spectra of 1-O-n-butanoyl-2,3:4,5-di-O-isopropylidenexylitol.

| C | δ (ppm) | H | δ (ppm) | | J (Hz) |
|---|---|---|---|---|---|
| $C_1$ | 63.9 | $H_{1a}$ | 4.28 | dd | $J_{1a-21b} = 11.0$ |
| $C_2$ | 75.3 | $H_{1b}$ | 4.07 | dd | $J_{1a-2} = 2.6$ |
| | | | | | $J_{1b-2} = 5.5$ |
| $C_3$ | 77.4 | $H_2$ | 4.12 | m | $J_{2-3} = 7.3$ |
| $C_4$ | 74.8 | $H_3$ | 3.85 | dd | $J_{3-4} = 4.5$ |
| $C_5$ | 65.4 | $H_4$ | 4.18 | ddd | $J_{4-5a} = 8.0$ |
| $C_{iso}$ | 109.9 | $H_{5a}$ | 4.03 | dd | $J_{5a-5b} = 7.7$ |
| $C_{iso}$ | 109.6 | $H_{5b}$ | 3.83 | dd | $J_{4-5b} = 6.7$ |
| $CH_3$ | 26.9 | $CH_{3\ iso}$ | 1.37 | s | — |
| $CH_3$ | 26.8 | $CH_{3\ iso}$ | 1.35 | s | — |
| $CH_3$ | 26.0 | $CH_{3\ iso}$ | 1.35 | s | — |
| $CH_3$ | 25.2 | $CH_{3\ iso}$ | 1.30 | s | — |
| $C_{1'}$ | 173.0 | $H_{2'}$ | 2.28 | t | $J_{2'-3'} = 7.4$ |
| $C_{2'}$ | 35.8 | $H_{3'}$ | 1.55 | q | $J_{3'-4'} = 7.3$ |
| $C_{3'}$ | 18.2 | $H_{4'}$ | 0.88 | t | — |
| $C_{4'}$ | 13.4 | | | | |

(Solvent: CDCl$_3$; chemical shift δ with respect to the TMS signal).

TABLE 11

$^1$H and $^{13}$C NMR spectra of 1-O-phenylacetyl-2,3:4,5-di-O-isopropylidenexylitol.

| C | δ (ppm) | H | δ (ppm) | | J (Hz) |
|---|---|---|---|---|---|
| $C_1$ | 64.4 | $H_{1a}$ | 4.21 | dd | $J_{1a-21b} = 11.0$ |
| $C_2$ | 77.4 | $H_{1b}$ | 4.01 | dd | $J_{1a-2} = 2.5$ |
| | | | | | $J_{1b-2} = 5.7$ |
| $C_3$ | 75.1 | $H_2$ | 4.04 | m | $J_{2-3} = 7.3$ |
| $C_4$ | 74.7 | $H_3$ | 3.71 | dd | $J_{3-4} = 3.9$ |
| $C_5$ | 65.5 | $H_4$ | 4.08 | ddd | $J_{4-5a} = 8.1$ |
| $C_{iso}$ | 110.0 | $H_{5a}$ | 3.88 | dd | $J_{5a-5b} = 7.2$ |
| $C_{iso}$ | 109.7 | $H_{5b}$ | 3.73 | dd | $J_{4-5b} = 6.7$ |
| $CH_3$ | 26.9 | $CH_{3\ iso}$ | 1.38 | s | — |
| $CH_3$ | 26.8 | $CH_{3\ iso}$ | 1.36 | s | — |
| $CH_3$ | 26.0 | $CH_{3\ iso}$ | 1.33 | s | — |
| $CH_3$ | 25.3 | $CH_{3\ iso}$ | 1.32 | s | — |
| $C_{1'}$ | 171.0 | $H_{2'}$ | 2.11 | s | — |
| $C_{2'}$ | 41.1 | $H_{4'}$ | 7.29 | m | — |
| $C_{3'}$ | 133.6 | $H_{5'}$ | to | | — |
| $C_{4'}$ | 129.2 | $H_{6'}$ | 7.15 | | — |
| $C_{5'}$ | 128.5 | | | | |
| $C_{6'}$ | 127.1 | | | | |

(Solvent: CDCl$_3$; chemical shift δ with respect to the TMS signal).

TABLE 12

$^1$H and $^{13}$C NMR spectra of 1-O-3'-phenylpropanoyl-2,3:4,5-di-O-isopropylidenexylitol.

| C | δ (ppm) | H | δ (ppm) | | J (Hz) |
|---|---|---|---|---|---|
| $C_1$ | 64.1 | $H_{1a}$ | 4.24 | dd | $J_{1a-21b} = 11.3$ |
| $C_2$ | 77.3 | $H_{1b}$ | 4.08 | dd | $J_{1a-2} = 2.7$ |
| | | | | | $J_{1b-2} = 6.5$ |
| $C_3$ | 75.2 | $H_2$ | 4.10 | m | $J_{2-3} = 7.9$ |
| $C_4$ | 74.8 | $H_3$ | 3.78 | dd | $J_{3-4} = 4.2$ |
| $C_5$ | 65.4 | $H_4$ | 4.13 | ddd | $J_{4-5a} = 8.1$ |
| $C_{iso}$ | 110.0 | $H_{5a}$ | 3.99 | dd | $J_{5a-5b} = 7.1$ |
| $C_{iso}$ | 109.7 | $H_{5b}$ | 3.79 | dd | $J_{4-5b} = 6.7$ |
| $CH_3$ | 26.9 | $CH_{3\ iso}$ | 1.37 | s | — |
| $CH_3$ | 26.9 | $CH_{3\ iso}$ | 1.36 | s | — |
| $CH_3$ | 26.0 | $CH_{3\ iso}$ | 1.35 | s | — |
| $CH_3$ | 25.3 | $CH_{3\ iso}$ | 1.31 | s | — |
| $C_{1'}$ | 172.4 | $H_{2'}$ | 2.92 | t | $J_{2'-3'} = 7.6$ |
| $C_{2'}$ | 35.6 | $H_{3'}$ | 2.65 | q | — |
| $C_{3'}$ | 30.8 | $H_{5'}$ | 7.27 | t | — |
| $C_{4'}$ | 140.2 | $H_{6'}$ | to | q | — |
| $C_{5'}$ | 128.4 | $H_{7'}$ | 7.14 | t | — |
| $C_{6'}$ | 128.1 | | | | |
| $C_{7'}$ | 126.2 | | | | |

(Solvent: CDCl$_3$; chemical shift δ with respect to the TMS signal).

TABLE 13

$^1$H and $^{13}$C NMR spectra of 1-O-4'-phenylbutanoyl-2,3:4,5-di-O-isopropylidenexylitol.

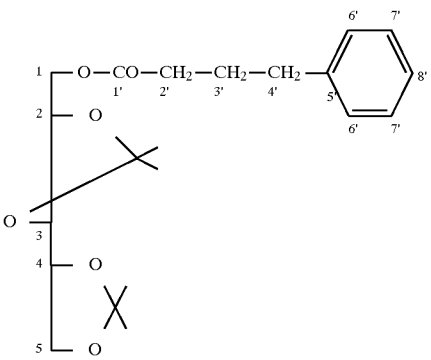

| C | δ (ppm) | H | δ (ppm) | | J (Hz) |
|---|---|---|---|---|---|
| $C_1$ | 64.1 | $H_{1a}$ | 4.26 | dd | $J_{1a-21b} = 11.2$ |
| $C_2$ | 77.4 | $H_{1b}$ | 4.07 | dd | $J_{1a-2} = 2.8$ |
| | | | | | $J_{1b-2} = 5.7$ |
| $C_3$ | 75.3 | $H_2$ | 4.13 | m | $J_{2-3} = 8.0$ |
| $C_4$ | 74.8 | $H_3$ | 3.84 | dd | $J_{3-4} = 4.4$ |
| $C_5$ | 65.5 | $H_4$ | 4.16 | ddd | $J_{4-5a} = 5.7$ |
| $C_{iso}$ | 110.0 | $H_{5a}$ | 4.02 | dd | $J_{5a-5b} = 7.8$ |
| $C_{iso}$ | 109.7 | $H_{5b}$ | 3.83 | dd | $J_{4-5b} = 6.7$ |
| $CH_3$ | 26.9 | $CH_{3\ iso}$ | 1.40 | s | — |
| $CH_3$ | 26.3 | $CH_{3\ iso}$ | 1.38 | s | — |
| $CH_3$ | 26.0 | $CH_{3\ iso}$ | 1.37 | s | — |
| $CH_3$ | 25.3 | $CH_{3\ iso}$ | 1.34 | s | — |
| $C_{1'}$ | 172.9 | $H_{2'}$ | 2.62 | t | $J_{2'-3'} = 7.6$ |
| $C_{2'}$ | 35.0 | $H_{3'}$ | 1.93 | q | $J_{3'-4'} = 7.5$ |
| $C_{3'}$ | 33.3 | $H_{4'}$ | 2.34 | t | — |
| $C_{4'}$ | 26.9 | $H_{6'}$ | 7.27 | m | — |
| $C_{5'}$ | 141.1 | $H_{7'}$ | to | | — |
| $C_{6'}$ | 128.3 | $H_{8'}$ | 7.12 | | — |
| $C_{7'}$ | 128.3 | | | | |
| $C_{8'}$ | 125.9 | | | | |

(Solvent: CDCl$_3$; chemical shift δ with respect to the TMS signal).

TABLE 14

$^1$H and $^{13}$C NMR spectra of 1-O-n-butanoyl-2,3-O-isopropylidenexylitol.

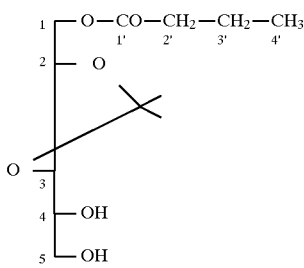

| C | δ (ppm) | H | δ (ppm) | | J (Hz) |
|---|---|---|---|---|---|
| $C_1$ | 65.8 | $H_{1a}$ | 4.26 | dd | $J_{1a-21b} = 11.6$ |
| $C_2$ | 77.2 | $H_{1b}$ | 4.08 | dd | $J_{1a-2} = 3.5$ |
| | | | | | $J_{1b-2} = 4.3$ |
| $C_3$ | 77.3 | $H_2$ | 4.20 | ddd | $J_{2-3} = 7.9$ |
| $C_4$ | 68.3 | $H_3$ | 3.83 | dd | $J_{3-4} = 3.0$ |
| $C_5$ | 64.7 | $H_4$ | 3.65 | ddd | $J_{4-5a} = 3.9$ |
| $C_{iso}$ | 109.5 | $H_{5a}$ | 3.74 | dd | $J_{5a-5b} = 12.0$ |
| $CH_3$ | 26.1 | $H_{5b}$ | 3.61 | dd | $J_{4-5b} = 4.0$ |
| $CH_3$ | 25.9 | $CH_{3\ iso}$ | 1.37 | s | — |
| $C_{1'}$ | 172.3 | $CH_{3\ iso}$ | 1.36 | s | — |
| $C_{2'}$ | 35.0 | $H_{2'}$ | 2.30 | t | $J_{2'-3'} = 7.3$ |
| $C_{3'}$ | 17.3 | $H_{3'}$ | 1.60 | q | $J_{3'-4'} = 6.3$ |

TABLE 14-continued $^1$H and $^{13}$C NMR spectra of 1-O-n-butanoyl-2,3-O-isopropylidenexylitol.

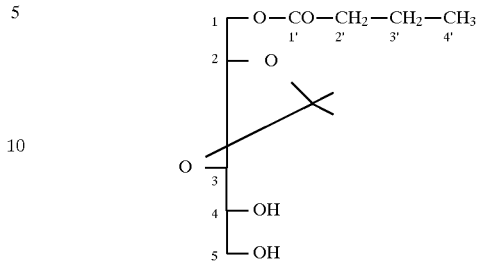

| C | δ (ppm) | H | δ (ppm) | | J (Hz) |
|---|---|---|---|---|---|
| $C_{4'}$ | 12.6 | $H_{4'}$ | 0.89 | t | — |
| | | $OH_{4,5}$ | 2.56 | s | — |

(Solvent: CDCl$_3$; chemical shift δ with respect to the TMS signal).

TABLE 15

$^1$H and $^{13}$C NMR spectra of 1-O-n-butanoylxylitol.

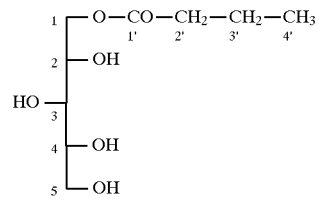

| C | δ (ppm) | H | δ (ppm) | | J (Hz) |
|---|---|---|---|---|---|
| $C_1$ | 66.9 | $H_{1a}$ | 4.52 | dd | $J_{1a-21b} = 11.1$ |
| $C_2$ | 72.3 | $H_{1b}$ | 4.47 | dd | $J_{1a-2} = 6.7$ |
| | | | | | $J_{1b-2} = 4.7$ |
| $C_3$ | 74.0 | $H_2$ | 4.36 | ddd | $J_{2-3} = 3.8$ |
| $C_4$ | 71.4 | $H_3$ | 4.25 | dd | $J_{3-4} = 5.5$ |
| $C_5$ | 64.4 | $H_4$ | 4.21 | m | $J_{4-5a} = 3.6$ |
| $C_{1'}$ | 173.0 | $H_{5a}$ | 4.09 | dd | $J_{5a-5b} = $ n.d. |
| $C_{2'}$ | 36.2 | $H_{5b}$ | 4.09 | dd | $J_{4-5b} = 6.0$ |
| $C_{3'}$ | 18.7 | $H_{2'}$ | 1.88 | t | $J_{2'-3'} = 7.3$ |
| $C_{4'}$ | 13.7 | $H_{3'}$ | 1.22 | q | $J_{3'-4'} = 7.3$ |
| | | $H_{4'}$ | 0.44 | t | — |
| | | $OH_{2-5}$ | 5.5–6.4 | m | — |

(Solvent: C$_5$D$_5$N; chemical shift δ with respect to the TMS signal).

TABLE 16

$^1$H and $^{13}$C NMR spectra of 1-O-phenylacetyl-2,3-O-isopropylidene-xylitol.

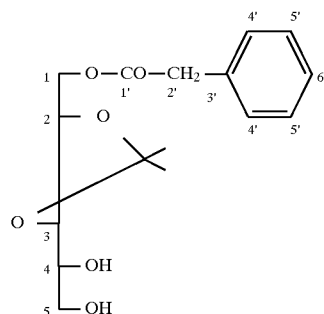

| C | δ (ppm) | H | δ (ppm) | | J (Hz) |
|---|---|---|---|---|---|
| $C_1$ | 64.5 | $H_{1a}$ | 4.28 | dd | $J_{1a-21b} = 11.5$ |
| $C_2$ | 74.9 | $H_{1b}$ | 4.12 | dd | $J_{1a-2} = 3.5$ |

TABLE 16-continued $^1$H and $^{13}$C NMR spectra of 1-O-phenylacetyl-2,3-O-isopropylidene-xylitol.

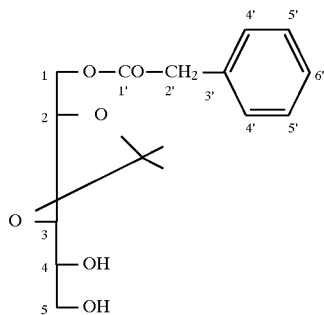

| C | δ (ppm) | H | δ (ppm) | | J (Hz) |
|---|---|---|---|---|---|
| | | | | | $J_{1b-2}$ = 4.5 |
| $C_3$ | 78.9 | $H_2$ | 4.19 | m | $J_{2-3}$ = 7.9 |
| $C_4$ | 69.7 | $H_3$ | 3.78 | dd | $J_{3-4}$ = 2.6 |
| $C_5$ | 64.0 | $H_4$ | 3.63 | ddd | $J_{4-5a}$ = n.d. |
| $C_{iso}$ | 109.9 | $H_{5a}$ | 3.60 | dd | $J_{5a-5b}$ = 8.0 |
| $CH_3$ | 26.9 | $H_{5b}$ | 3.53 | dd | $J_{4-5b}$ = 3.9 |
| $CH_3$ | 26.8 | $CH_{3\ iso}$ | 1.33 | s | — |
| $C_{1'}$ | 171.2 | $CH_{3\ iso}$ | 1.35 | s | — |
| $C_{2'}$ | 41.1 | $H_{2'}$ | 2.37 | s | — |
| $C_{3'}$ | 133.6 | $H_{4'}$ | 7.30 | m | — |
| $C_{4'}$ | 129.2 | $H_{5'}$ | to | | — |
| $C_{5'}$ | 128.5 | $H_{6'}$ | 7.22 | | — |
| $C_{6'}$ | 127.1 | $OH_{4,5}$ | 2.7 | m | — |

(Solvent: $CDCl_3$; chemical shift δ with respect to the TMS signal).

TABLE 17

$^1$H and $^{13}$C NMR spectra of 1-O-phenylacetylxylitol.

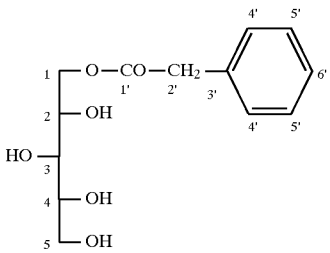

| C | δ (ppm) | H | δ (ppm) | | J (Hz) |
|---|---|---|---|---|---|
| $C_1$ | 67.8 | $H_{1a}$ | 4.75 | dd | $J_{1a-21b}$ = 11.2 |
| $C_2$ | 72.6 | $H_{1b}$ | 4.70 | dd | $J_{1a-2}$ = 7.3 |
| | | | | | $J_{1b-2}$ = 4.8 |
| $C_3$ | 74.2 | $H_2$ | 4.56+ | m | $J_{2-3}$ = 3.7 |
| $C_4$ | 71.6 | $H_3$ | 4.43 | dd | $J_{3-4}$ = 4.8 |
| $C_5$ | 64.8 | $H_4$ | 4.40 | ddd | $J_{4-5a}$ = 3.1 |
| $C_{1'}$ | 172.1 | $H_{5a}$ | 4.26 | dd | $J_{5a-5b}$ = n.d. |
| $C_{2'}$ | 41.7 | $H_{5b}$ | 4.21 | dd | $J_{4-5b}$ = 5.1 |
| $C_{3'}$ | 135.4 | $H_{2'}$ | 1.94 | s | — |
| $C_{4'}$ | 130.2 | $H_{4'}$ | 7.33 | m | — |
| $C_{5'}$ | 129.2 | $H_{5'}$ | to | | — |
| $C_{6'}$ | 127.6 | $H_{6'}$ | 7.13 | | — |
| | | $OH_{2,5}$ | 6.11 | m | — |

(Solvent: $C_5D_5N$; chemical shift δ with respect to the TMS signal).

TABLE 18

$^1$H and $^{13}$C NMR spectra of 1-O-3'-phenylpropanoyl-2,3-O-isopropylidenexylitol.

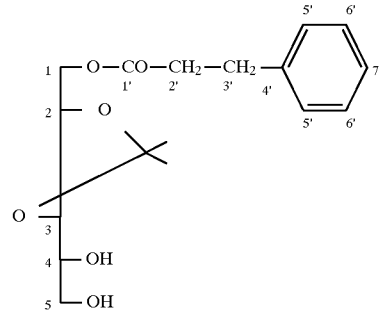

| C | δ (ppm) | H | δ (ppm) | | J (Hz) |
|---|---|---|---|---|---|
| $C_1$ | 64.5 | $H_{1a}$ | 4.29 | dd | $J_{1a-21b}$ = 11.2 |
| $C_2$ | 75.1 | $H_{1b}$ | 4.16 | dd | $J_{1a-2}$ = 3.6 |
| | | | | | $J_{1b-2}$ = 1.4 |
| $C_3$ | 77.9 | $H_2$ | 4.23 | m | $J_{2-3}$ = 7.3 |
| $C_4$ | 69.8 | $H_3$ | 3.82 | dd | $J_{3-4}$ = 3.0 |
| $C_5$ | 63.7 | $H_4$ | 3.69 | ddd | $J_{4-5a}$ = 7.0 |
| $C_{iso}$ | 110.0 | $H_{5a}$ | 3.71 | dd | $J_{5a-5b}$ = 7.9 |
| $CH_3$ | 26.8 | $H_{5b}$ | 3.63 | dd | $J_{4-5b}$ = 4.3 |
| $CH_3$ | 26.4 | $CH_{3\ iso}$ | 1.38 | s | — |
| $C_{1'}$ | 172.4 | $CH_{3\ iso}$ | 1.36 | s | — |
| $C_{2'}$ | 35.5 | $H_{2'}$ | 2.91 | t | $J_{2'-3'}$ = 7.7 |
| $C_{3'}$ | 30.7 | $H_{3'}$ | 2.64 | t | — |
| $C_{4'}$ | 140.2 | $H_{5'}$ | 7.27 | m | — |
| $C_{5'}$ | 128.4 | $H_{6'}$ | to | | — |
| $C_{6'}$ | 128.2 | $H_{7'}$ | 7.14 | | — |
| $C_{7'}$ | 126.2 | $OH_{4,5}$ | 4.16 | m | — |

(Solvent: $CDCl_3$; chemical shift δ with respect to the TMS signal).

TABLE 19

$^1$H and $^{13}$C NMR spectra of 1-O-(3'-phenylpropanoyl)xylitol.

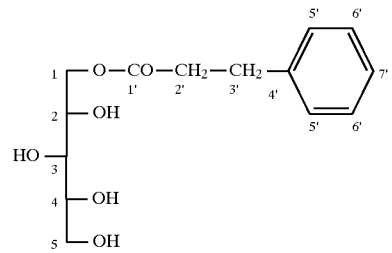

| C | δ (ppm) | H | δ (ppm) | | J (Hz) |
|---|---|---|---|---|---|
| $C_1$ | 67.4 | $H_{1a}$ | 4.66 | dd | $J_{1a-21b}$ = 10.7 |
| $C_2$ | 72.6 | $H_{1b}$ | 4.63 | dd | $J_{1a-2}$ = 7.2 |
| | | | | | $J_{1b-2}$ = 4.5 |
| $C_3$ | 74.3 | $H_2$ | 4.49 | m | $J_{2-3}$ = 3.7 |
| $C_4$ | 71.7 | $H_3$ | 4.38 | dd | $J_{3-4}$ = 4.9 |
| $C_5$ | 64.8 | $H_4$ | 4.36 | ddd | $J_{4-5a}$ = 3.3 |
| $C_{1'}$ | 173.3 | $H_{5a}$ | 4.22 | dd | $J_{5a-5b}$ = n.d. |
| $C_{2'}$ | 36.3 | $H_{5b}$ | 4.18 | dd | $J_{4-5b}$ = 5.6 |
| $C_{3'}$ | 30.9 | $H_{2'}$ | 2.87 | t | $J_{2'-3'}$ = 7.7 |
| $C_{4'}$ | 141.6 | $H_{3'}$ | 2.60 | t | — |
| $C_{5'}$ | 129.2 | $H_{5'}$ | 7.23 | m | — |
| $C_{6'}$ | 129.0 | $H_{6'}$ | to | | — |
| $C_{7'}$ | 126.9 | $H_{7'}$ | 7.09 | | — |
| | | $OH_{2,5}$ | 6.04 | m | — |

(Solvent: $C_5D_5N$; chemical shift δ with respect to the TMS signal).

TABLE 20

$^1$H and $^{13}$C NMR spectra of 1-O-4'-phenylbutanoyl-2,3-O-isopropylidenexylitol.

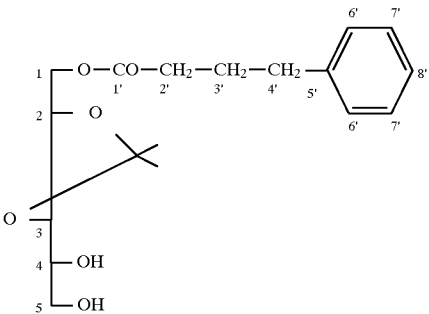

| C | δ (ppm) | H | δ (ppm) | | J (Hz) |
|---|---|---|---|---|---|
| $C_1$ | 64.4 | $H_{1a}$ | 4.44 | dd | $J_{1a-21b} = 11.2$ |
| $C_2$ | 75.2 | $H_{1b}$ | 4.10 | dd | $J_{1a-2} = 3.5$ |
| | | | | | $J_{1b-2} = 5.3$ |
| $C_3$ | 78.8 | $H_2$ | 4.21 | m | $J_{2-3} = 8.0$ |
| $C_4$ | 70.0 | $H_3$ | 3.84 | dd | $J_{3-4} = 2.0$ |
| $C_5$ | 63.8 | $H_4$ | 3.68 | ddd | $J_{4-5a} = $ n.d. |
| $C_{iso}$ | 110.0 | $H_{5a}$ | 3.68 | dd | $J_{5a-5b} = 3.2$ |
| $CH_3$ | 26.8 | $H_{5b}$ | 3.65 | dd | $J_{4-5b} = $ n.d. |
| $CH_3$ | 26.2 | $CH_{3\ iso}$ | 1.38 | s | — |
| $C_{1'}$ | 173.1 | $CH_{3\ iso}$ | 1.36 | s | — |
| $C_{2'}$ | 35.0 | $H_{2'}$ | 2.60 | t | $J_{2'-3'} = 7.5$ |
| $C_{3'}$ | 33.3 | $H_{3'}$ | 1.93 | q | $J_{3'-4'} = 7.6$ |
| $C_{4'}$ | 26.9 | $H_{4'}$ | 2.32 | t | — |
| $C_{5'}$ | 141.1 | $H_{6'}$ | 7.26 | m | — |
| $C_{6'}$ | 128.3 | $H_{7'}$ | to | | — |
| $C_{7'}$ | 128.3 | $H_{8'}$ | 7.11 | | — |
| $C_{8'}$ | 125.9 | $OH_{4,5}$ | 4.15 | m | — |

(Solvent: $CDCl_3$; chemical shift δ with respect to the TMS signal).

TABLE 21

$^1$H and $^{13}$C NMR spectra of 1-O-(4'-phenylbutanoyl)xylitol.

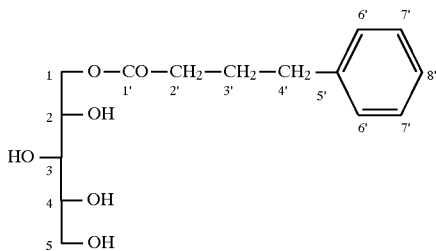

| C | δ (ppm) | H | δ (ppm) | | J (Hz) |
|---|---|---|---|---|---|
| $C_1$ | 67.3 | $H_{1a}$ | 4.75 | dd | $J_{1a-21b} = 11.2$ |
| $C_2$ | 72.6 | $H_{1b}$ | 4.69 | dd | $J_{1a-2} = 7.2$ |
| | | | | | $J_{1b-2} = 4.5$ |
| $C_3$ | 74.3 | $H_2$ | 4.56 | m | $J_{2-3} = 3.7$ |
| $C_4$ | 71.7 | $H_3$ | 4.43 | dd | $J_{3-4} = 5.0$ |
| $C_5$ | 64.8 | $H_4$ | 4.40 | ddd | $J_{4-5a} = 3.5$ |
| $C_{1'}$ | 173.9 | $H_{5a}$ | 4.28 | dd | $J_{5a-5b} = $ n.d. |
| $C_{2'}$ | 35.6 | $H_{5b}$ | 4.22 | dd | $J_{4-5b} = 5.4$ |
| $C_{3'}$ | 34.6 | $H_{2'}$ | 2.52 | t | $J_{2'-3'} = 7.7$ |
| $C_{4'}$ | 27.3 | $H_{3'}$ | 1.87 | q | $J_{3'-4'} = 7.0$ |
| $C_{5'}$ | 142.4 | $H_{4'}$ | 2.30 | t | — |
| $C_{6'}$ | 129.2 | $H_{6'}$ | 7.25 | m | — |
| $C_{7'}$ | 129.1 | $H_{7'}$ | to | | — |
| $C_{8'}$ | 126.6 | $H_{8'}$ | 7.10 | | — |
| | | $OH_{2,5}$ | 5.92 | m | — |

(Solvent: $C_5D_5N$; chemical shift δ with respect to the TMS signal).

We claim:

1. A monoester of a carboxylic acid selected from the group consisting of phenylacetic acid, 3-phenylpropionic acid, 4-phenylbutyric acid and n-butyric acid and a member selected from the group consisting of monosaccharides and sugar alcohols of the formula $Su(OH)_5$, said monoester having the formula:

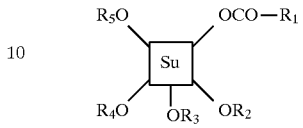

wherein $R_1CO$ is the acyl of the carboxylic acid, $R_2$, $R_3$, $R_4$ and $R_5$ are individually selected from the group consisting of hydrogen, optionally unsaturated, optionally cyclic hydrocarbons or $R_2$ and $R_3$ or $R_4$ and $R_5$ form an acetal

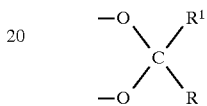

with $R-C-R^1$ being selected from the group consisting of phenylmethylene, methylene, cyclohexylidene and isopropylidene with at least two of $R_2$, $R_3$, $R_4$ and $R_5$ being hydrogen and $Su(OH)_5$ or said corresponding monoester has a structure that prevents internal transesterification and the ester is bonded to an anomeric carbon atom or a $C_1$ primary carbon atom, with the proviso that when $R_1CO$ is n-butanoyl, the monosaccharide or itol is other than D-galactose or D-glucose or glycerol.

2. A monoester of claim 1 wherein $Su(OH)_5$ precursor is selected from the group consisting of D-mannose and xylitol.

3. A monoester of claim 2 selected from the group consisting of 1-O-acyl-2,3-O-acetal-xylitol and 1-O-acyl-xylitol and the acyl is derived from a carboxylic acid selected from the group consisting of phenylacetic acid, 3-phenylpropionic acid, 4-phenylbutyric acid and n-butyric acid.

4. A monoester of claim 1 wherein $R_2$ and $R_3$ or $R_4$ and $R_5$ form an acetal and R and R' together with the carbon to which they are attached form a member selected from the group consisting of phenylmethylene, methylene, cyclohexylidene and isopropylidene.

5. A monoester of claim 1 selected from the group consisting of α- and β-O-acyl-2,3-acetal of D-mannosides and α-and β-O-acyl-D-mannosides and the acyl is derived from a carboxylic acid selected from the group consisting of phenylacetic acid, 3-phenylpropionic acid, 4-phenylbutyric acid and n-butyric acid.

6. A monoester of claim 1 selected from the group consisting of α-O-n-butanoyl-D-mannoside and α-O-n-butanoyl-2,3,O-isopropylidene-D-mannoside.

7. A monoester of claim 1 selected from the group consisting of α-O-phenylacetyl-D-mannoside and α-O-phenylacetyl-2,3-O-isopropylidene-D-mannoside.

8. A monoester of claim 1 selected from the group consisting of α-O-3'-phenylpropanoyl-D-mannoside and a α-O-3'-phenylpropanoyl-2,3-O-isopropylidene-D-mannoside.

9. A monoester of claim 1 selected from the group consisting of α-O-4-phenylbutanoyl-D-mannoside and α-O-4-phenylbutanoyl-2,3-O-isopropylidene-D-mannoside.

10. A monoester of claim 1 selected from the group consisting of 1-O-n-butanoyl-xylitol and 1-O-n-butanoyl-2,3-O-isopropylidene-xylitol.

11. A monoester of claim 1 selected from the group consisting of 1-O-phenylacetyl-xylitol and 1-O-phenylacetyl-2,3-O-isopropylidene-xylitol.

12. A monoester of claim 1 selected from the group consisting of 1-O-(3-phenylpropanoyl)-xylitol and 1-O-(3-phenylpropanoyl)-2,3-O-isopropylidene-xylitol.

13. A monoester of claim 1 selected from the group consisting of 1-O-(4-phenylbutanoyl)-xylitol and 1-O-(4-phenylbutanoyl)-2,3-O-isopropylidene-xylitol.

14. A method of treating heamoglobin insufficiencies in warm-blooded animals comprising administering to warm-blooded animals in need thereof an amount of a monoester of claim 1 sufficient to treat heamoglobin insufficiency.

15. The method of claim 14 wherein the $Su(OH)_5$ precursor is selected from the group consisting of D-mannose and xylitol.

16. A method of treating premalignant and malignant tumors in warm-blooded animals comprising administering to warm-blooded animals in need thereof an amount of a monoester of claim 1 sufficient to treat said tumors.

17. The method of claim 16 wherein the $Su(OH)_5$ precursor is selected from the group consisting of D-mannose and xylitol.

\* \* \* \* \*